United States Patent [19]

Gabbay

[11] Patent Number: 4,759,758
[45] Date of Patent: Jul. 26, 1988

[54] PROSTHETIC HEART VALVE

[76] Inventor: Shlomo Gabbay, 57 Birchwood La., Hartsdale, N.Y. 10530

[21] Appl. No.: 679,261

[22] Filed: Dec. 7, 1984

[51] Int. Cl.$^4$ ............................................... A61F 2/24
[52] U.S. Cl. ......................................... 623/2; 623/900
[58] Field of Search ................ 3/1.5, 1 C, 1.4; 623/2, 623/900

[56] References Cited

U.S. PATENT DOCUMENTS

| | | | |
|---|---|---|---|
| 3,562,820 | 2/1971 | Braun | 3/1.4 |
| 3,755,823 | 9/1973 | Hancock | 623/900 X |
| 4,084,268 | 4/1978 | Ionescu et al. | 3/1.5 |
| 4,106,129 | 8/1978 | Carpentier et al. | 623/900 X |
| 4,218,783 | 8/1980 | Reul et al. | 3/1.5 |
| 4,275,469 | 6/1981 | Gabbay | 3/1.5 |
| 4,535,483 | 8/1985 | Klawitter et al. | 623/2 |
| 4,629,459 | 12/1986 | Ionescu et al. | 623/2 |

Primary Examiner—Richard J. Apley
Assistant Examiner—Alan W. Cannon
Attorney, Agent, or Firm—Jordan B. Bierman

[57] ABSTRACT

An improved prosthetic heart valve comprises a support body or stent covered by a layer of biological tissue having only the smooth surfaces thereof presented outwardly. The stent has a cutaway section and a flexible cusp sewn thereto for opening and closing the valve. The valve cusp is made of pericardial tissue which has been doubled over such that the rough side thereof is folded inwardly. A sewing ring is secured around the base of the stent and is made of pericardial or other biological material, so as to increase the likelihood of the sewing ring becoming covered with epithelium. The smooth-surfaced biological construction of the valve is highly durable and reduces the risk of thrombogenic or infection sites.

13 Claims, 4 Drawing Sheets

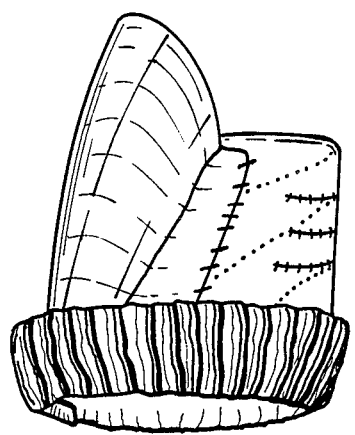
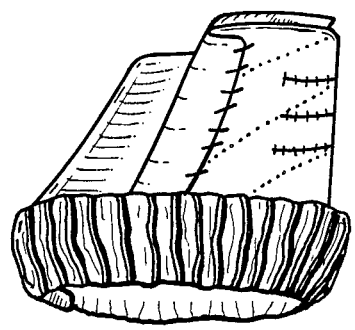
FIG. 9    FIG. 10
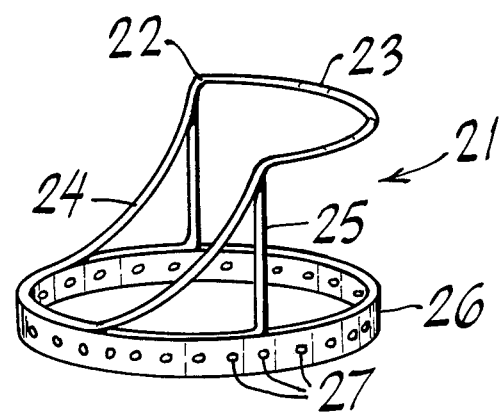
FIG. 11

PROSTHETIC HEART VALVE

FIELD OF THE INVENTION

This invention relates to prosthetic valves for regulating blood flow and more particularly to a prosthetic heart valve.

DESCRIPTION OF THE PRIOR ART

In the field of heart valves, conventional prosthetic valves have problems with turbulence which restricts the flow of blood and may cause blood clots, irritation or scarring of the heart wall, or clicking sounds of the valve which can be uncomfortable or disturbing. In U.S. Pat. No. 4,275,469, I disclosed an improved prosthetic heart valve consisting of an open wire frame or a tubular membrane having a flexible inlet end to be attached to the annulus of a heart and an outlet end having an extended single flap or cusp adapted to move toward and away from the membrane wall so as to close or open the valve at the outlet end. I have also disclosed an improved form of two-cusp heart valve maintained by a semiflexible support ring which closely simulates a natural heart valve, in my copending U.S. application Ser. No. 841,791, filed Oct. 13, 1977, now U.S. Pat. No. 4,491,986.

However, these and other known forms of heart valves have the problem that areas made of exposed synthetic material, such as the sewing ring by which the valve is attached to the heart wall, remain uncovered and are not endothelialized, i.e., enveloped in biological tissue. One reason for this phenomenon is that synthetic material tends to reject coverage by living tissue, i.e. epithelium, or have collecting surfaces that become thrombogenic sites. I have also found that even biological tissue, such as pericardium, which has a rough surface on one side that is usually facing inwardly of the valve in the blood flow area, has the risk of sites on the rough areas tending to cause formation of blood clots leading to thromboembolisms. A related problem is a relatively high incidence of infection (endocarditis) due to bacterial growth or accumulation of vegetation at such collecting sites. In particular, I have found that the use of pericardial tissue, having a rough side oriented in the blood flow area, presents a risk of infection or thrombogenesis due to platelet accumulation or vegetation growth on the rough surface.

Accordingly, it is a principal object of the invention to provide a prosthetic heart valve which is constructed and made of materials so as to minimize thrombogenic risk. It is a further object to provide a heart valve which has a reduced risk of infection, and is flexible, durable and can function for a long time without failure.

SUMMARY OF THE INVENTION

In accordance with my invention, an improved prosthetic heart valve has a supporting frame or stent of flexible and durable construction which is covered by biological tissue, such as pericardial material, and has a flap or cusp formed from pericardial material which is folded over so as to present only the smooth surfaces thereof outwardly in the blood flow area.

The stent is preferably cylindrical in shape and has a cutaway portion at its outlet end which is shaped to accommodate a flap or cusp of the valve suitably in its open or closed positions. The edge of the cutaway portion is preferably lined with a strip of silicone, one or more layers of pericardium, or other supporting material to reduce the possibility of tearing or fracturing along the edge. The cusp, made from the doubled-over biological tissue, is sewn to the pericardium-covered stent along the edges of the cutaway portion. The cusp and cutaway portion are dimensioned so as to allow complete closure of the blood flow area in the closed position. A sewing ring is provided at the inlet end of the valve and is made of pericardial or other biological tissue, or of dacron material impregnated with collagen or any other biologically acceptable material.

DESCRIPTION OF THE DRAWINGS

The above objects and further features and advantages of the invention are described in detail below in conjunction with the drawings, of which:

FIG. 9 shows the assembled heart valve in the open position;

FIG. 10 shows the heart valve in the closed position; and

FIG. 11 is a perspective view of a wire frame support in accordance with another embodiment of the invention.

DETAILED DESCRIPTION OF THE INVENTION

Figure 1:
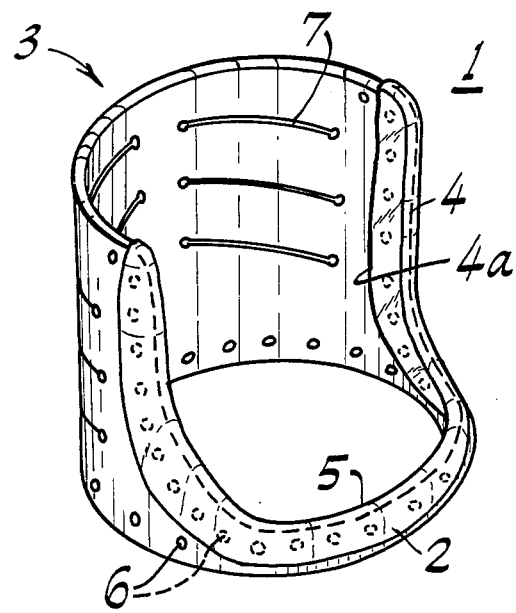
FIG. 1 is a perspective view of a stent in accordance with one embodiment of the invention.
Figure 2:
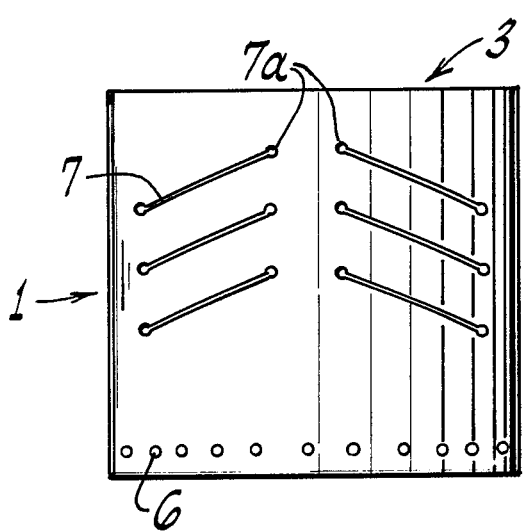
FIG. 2 is a front view of the stent of FIG. 1.
Figure 3:
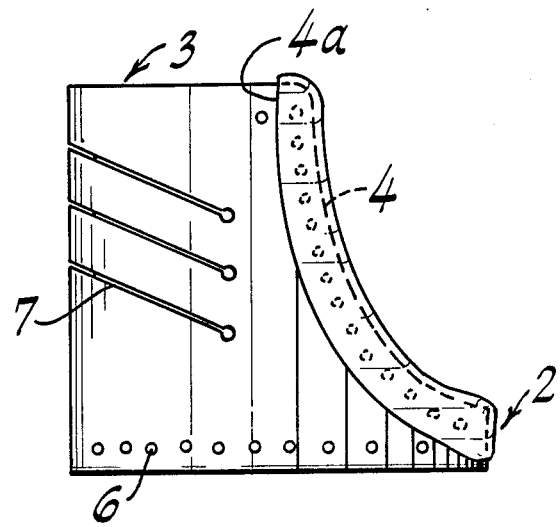
FIG. 3 is a side view of the stent of FIG. 1.

The following is a description of the preferred embodiments of the invention, and is intended only to be illustrative of the principles of the invention without limitation. In the drawings, like parts are referenced by the same reference numerals.

Referring to FIG. 1, a support body or stent 1 is made of a flexible material, preferably a plastic such as Delrin or Teflon material, and has a generally right cylindrical form with substantially the same diameter throughout. Lower annular portion 2 constitutes an inlet end for the valve and forms a base for attachment of the valve to the annulus of a heart. Upper portion 3 of stent 1 includes a cylindrical portion over approximately half the circumference and a cutaway section over the remainder. The cutaway section is defined by downwardly curving edges 4 ending in horizontal edge 5 coplanar with base 2. A rounded corner is formed where curved edges 4 join the edges of upper portion 3, to avoid the possibility of tearing of tissue. Stent 1 has a plurality of sewing holes 6 and slits 7 for attaching a layer of covering tissue to the stent, as will be described further herein. Slits 7 terminate in round holes 7a which spread the stress forces at the ends of the slits so as to prevent fracturing of the plastic material after repeated flexing when the valve is used. A backing strip 4a of silicone, single or double layer strip of pericardium, or any other resilient material may be used to trim curved edge 4, in order to prevent tearing of the tissue which is attached thereto.

Figure 4:
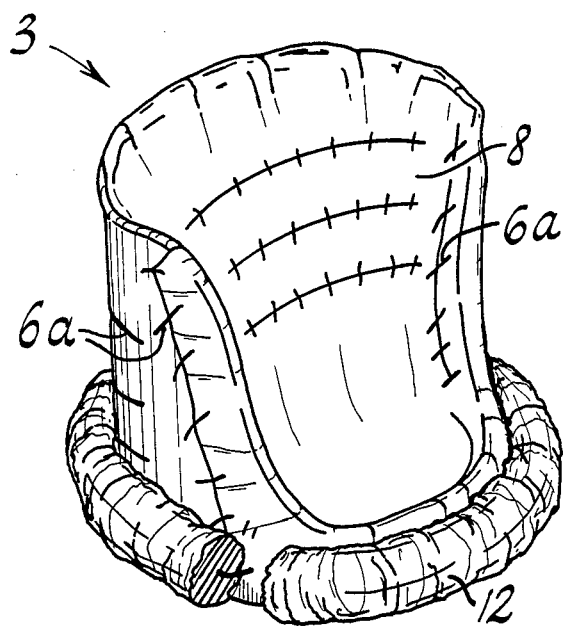
FIG. 4 is a perspective view of the stent covered with pericardial material and having a sewing ring, in accordance with the invention.
Figure 5:
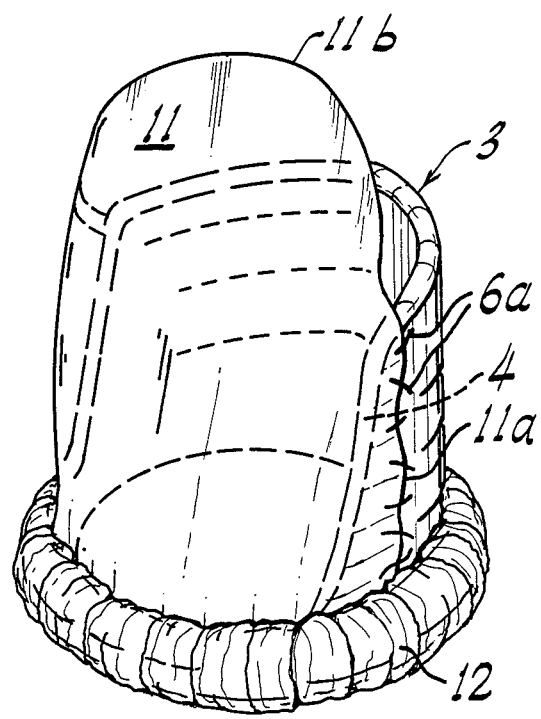
FIG. 5 is a perspective view of a complete assembly of the prosthetic heart valve of the invention.
Figure 8:
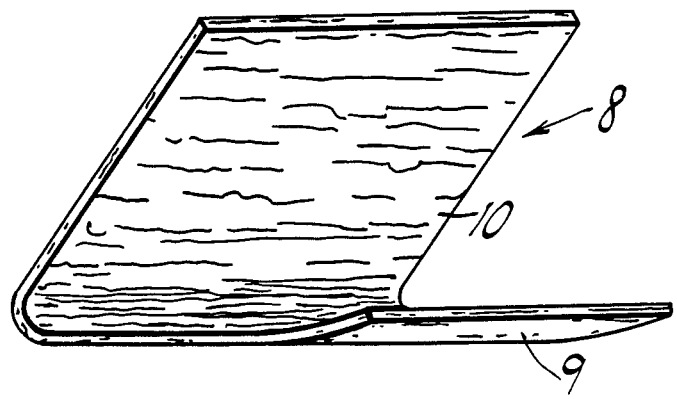
FIG. 8 is a close-up view of the smooth and rough surfaces of pericardial tissue.

In order to minimize the exposure of synthetic surfaces to the blood flow and the creation of possible thrombogenic sites, the stent is covered with one or more layers of biological tissue such as pericardial tissue 8, which has a rough side 10 and a smooth side 9 as shown in FIG. 8. Referring to FIGS. 4 and 5, the pericardial tissue 8 is folded over the supporting wall of the stent, and sewn to the stent along downwardly curving edges 4, around the circumferential base 2, and through slits 7.

A cusp or flap 11 for the heart valve is then sewn to the cutaway section of the stent by its lower edges 11a to the sewing holes extending along downwardly curving edges 4 of the stent. The flap is formed from biological tissue such as pericardium which has a rough side and a smooth side. Rough side 10 can form collecting sites for bacteria and other vegetation which increases the risk of infection and can result ultimately in calcification. In the invention, the pericardial tissue is doubled over so that the rough side is folded inward and only the smooth sides 9 are exposed outwardly to the blood flow area and to the heart wall in contact with the exterior of the valve. The doubled-over pericardium also provides a double thickness, and thus is stronger and increases resistence to fatigue, tearing, or other failure of the valve. A glue, such as fibrin glue, may be applied to bond the inner surfaces for a more cohesive cusp structure. The upper part 11b of flap 11 extends above upper portion 3 of the stent. When the valve functions so as to assume its closed position, the upper part 11b collapses against the inner wall of upper portion 3, as shown in FIG. 10, to thereby close the blood flow passage through the valve. In the open position, flap 11 returns to its upwardly standing position by the blood flow movement through the valve.

The flap 11 is preferably made from a biological material such as bovine pericardium (the membrane surrounding the heart of a calf or other animals). The pericardium is preferably treated with gluteraldehyde which fixes the tissue so that it is inert and not subject to rejection by immunologic response of the human body. The treatment is applied to the pericardium in a mold in order to set the material to the desired curved shape for use in the valve, as shown in the closed position of FIG. 10. The material is extremely strong and flexible and has a high modulus of elasticity so that the valve can be continuously opened and closed with the membrane retaining its original shape. Other biologically acceptable materials include dura mater which is the membrane surrounding the human brain or that of animals such as pigs, sheep and calves.

Figure 6:
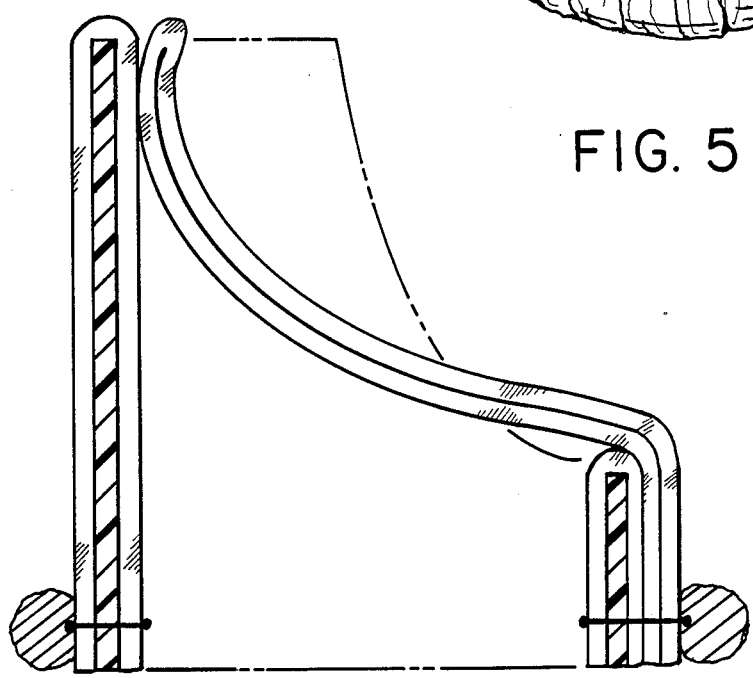
FIG. 6 is a sectional side view of the assembled heart valve in the closed position.

The heart valve 1 also has a cuff or sewing ring 12 extending circumferentially around base 2 of the stent, and is fixed in position by sewing through sewing holes 6, as shown in FIG. 6. Preferably, sewing ring 12 is made of pericardial tissue or other biological material, or dacron impregnated with collagen or other biologically acceptable material. The use of the above-described valve construction of pericardium, biological tissue, or biologically treated material results effectively in a totally biological heart valve, with smooth surfaces throughout, which reduces the possibility that the valve, when attached to the heart, will have unendothelialized areas or will develop thrombogenic or infection sites.

Figure 7:
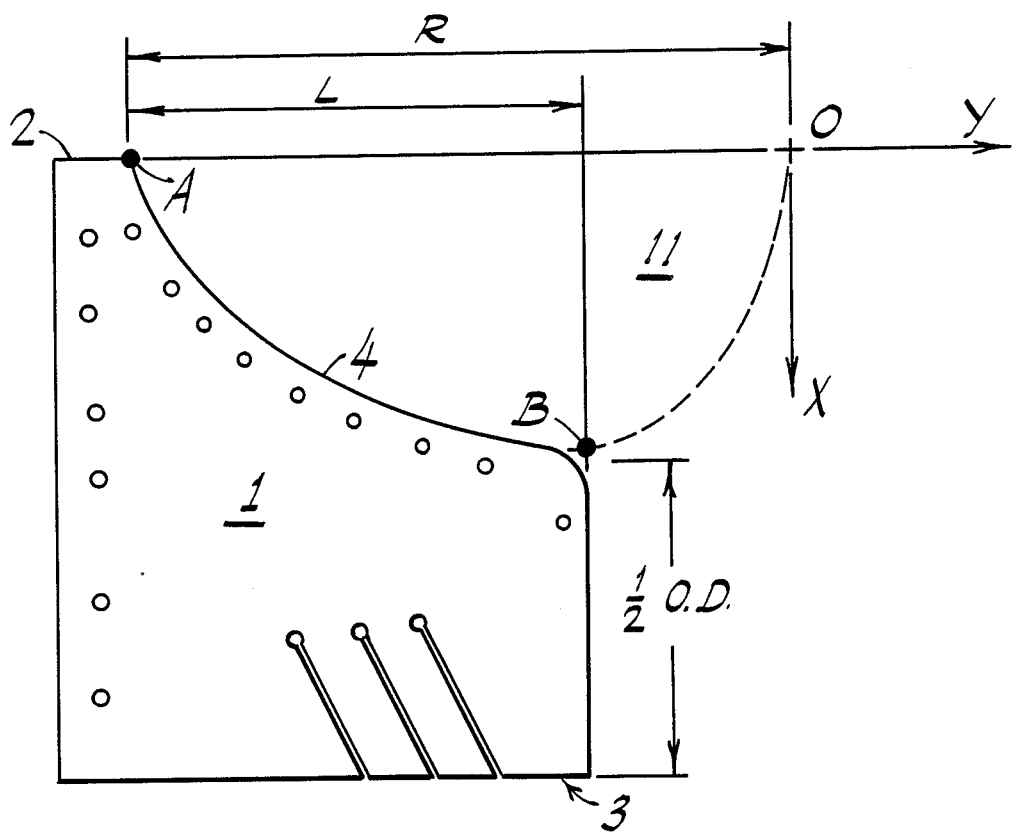
FIG. 7 is a schematic drawing showing a preferred geometry of the stent profile.

Referring to FIG. 7, a preferred geometric profile for the curved edges 4 of the stent is shown. In the drawing, the longitudinal direction of the stent is indicated on the Y-axis, and the transverse direction on the X-axis. The preferred curvature for edges 4, indicated by arc A-B, is a substantially elliptical curve having its center at O, which is the uppermost point of the flap 11 attached to stent 1 (shown in phantom lines). R indicates a radius of the ellipse extending between point O and point A. L indicates the linear distance from point A to the upper edge of the stent. O.D. indicates the outer diameter of the stent, and the distance extending from point B to the edge of the stent wall is selected to be generally one half of the outer diameter. A particularly preferred geometric profile for the curved edges 4 is given by the following relation:

$$\frac{4X^2 + Y^2}{R^2} = 1$$

and $$R = \frac{L^2 + O.D.^2}{2L}$$

With this profile, the flap 11 sewn to the curved edges 4 of stent 1 is properly located for collapsing against the inner wall of the stent to close the valve. In FIGS. 9 and 10, the assembled valve is shown in the open and closed positions.

The prosthetic valve of the invention thus has a durable construction with smooth surfaces formed by the double-folded cusp of biological tissue and a sewing ring of biological or biologically treated material. This totally biological and smooth-surfaced valve construction reduces the possibility of infection through bacterial growth or vegetation forming on rough surfaces or areas not covered with epithelium. The specified profile for the cutaway portion of the stent provides a proper dimensioning for complete closure of the valve by the cusp. Although the prosthetic valve is particularly suitable as a heart valve, it may also be used as an arterial or venous valve.

This improved prosthetic valve using a single layer cusp has been tested and found to be even more durable than any other conventional biological valve. In mechanical stress tests, which are about 10 times more stressful than normal use, the improved valve lasted far in excess of 200 million cycles. Further, in tests in animals, the improved valve showed a minimal incidence of infection or thromobogenesis. The valve of this invention using a double layer cusp would have an even greater durability in addition to further reduction of thrombogenic risk.

Another particularly advantageous feature of the invention is the improved method of storing the valve in alcohol, or other antiseptic solution which is not harmful to the human body, prior to its installation in the body. The conventional method is to store a prosthetic valve in glutaraldehyde, and requires about 5 hours to wash out the valve prior to installation since the glutaraldehyde can cause calcification of the valve in the body. By storing the valve in alcohol, it can be simply washed with water just prior to installation.

Another embodiment of the invention employs an open wire frame for the valve, as shown in U.S. Pat. No. 4,275,469, for example, instead of the stent of FIG. 1. Referring to FIG. 11, a support body 21 for the valve has a rounded wire frame 22 including curved rails 24, a half circumferential upper rim 23, and side braces 25 which are formed together integrally. The frame 22 is attached to lower band 26 which has sewing holes 27. Pericardial material is folded over the frame 22, with its smooth side facing outward, and secured to band 26, and a cuff is sewn circumferentially around the band, so as to form a valve body construction similar to that shown in and described with respect to FIG. 4 above. Pericardial material is then doubled over to form the smooth surfaced cusp, which is then secured to the valve body along curved rails 24 and band 26. The curvature of rails 24 is preferably substantially an ellipse of the dimensions given previously, for an optimal configuration of the cusp in closing the valve body.

Although these particular embodiments of the invention have been described, there are many other variations and modifications of the principles of the invention which would occur to one skilled in the art, including the substitution of equivalent materials, parts, or steps. All such variations and modifications are intended to be encompassed within the scope of the invention, as defined in the appended claims.

I claim:

1. A prosthetic valve comprising a support body of generally cylindrical shape having a lower circumferential base portion, an upper portion extending over at least half of a circumference thereof and a cutaway section defined over the remaining circumference thereof, the body having edges extending curvilinearly along the cutaway section from the upper portion to the base portion, a plurality of sewing holes formed in the body, a covering of biological tissue secured to the body through the sewing holes which has only smooth surfaces thereof presented outwardly, a flexible flap of biological tissue of opening and closing the valve having a lower portion secured to said curved edges and to said base portion, and an upper portion of the flap extending beyond the upper portion of the body, said flap and said cutaway section of the body being dimensioned such that the flap can be collapsed to a closed position against an inner wall of the body to close the valve, said flap being made of pericardial tissue doubled over, such that a rough side thereof is folded inwardly and only a smooth side thereof is presented outwardly.

2. The prosthetic valve of claim 1 further comprising a sewing ring extending circumferentially around the base portion and being made of pericardial tissue, biological tissue, or dacron tissue impregnated with collagen material.

3. The prosthetic valve of claim 1, wherein said flap is formed dura mater.

4. The prosthetic valve of claim 1, wherein said curved edges have an elliptical cross-section defined by an ellipse of the following relation:

$$\frac{4X^2 + Y^2}{R^2} = 1$$

$$R = \frac{L^2 + O.D.^2}{2L}$$

wherein R is the length of the flap from its upper portion to its lower portion at the base of the body;

L is the length from the intersection of the base with the curved edge to the upper portion of the body;

O.D. is the outer diameter of the cylindrical body;

X is the coordinate of the ellipse in the transverse direction of the body along the curved edge; and Y is the coordinate of the ellipse in the longitudinal direction of the body along the curved edge.

5. The prosthetic valve of claim 1, wherein said covering is made of pericardial tissue folded over said upper portion of the body and secured thereto through said sewing holes.

6. The prosthetic valve of claim 1, wherein said body is a cylinderically shaped stent made of synthetic material.

7. The prosthetic valve of claim 1, wherein said body comprises an open wire frame constituting said upper portion, cutaway section, and curved edges, and a lower band mounted to the wire frame and having a plurality of sewing holes therein.

8. The prosthetic valve of claim 1, further comprising a reinforcing strip secured to at least the curved edges of the support body.

9. The prosthetic valve of claim 8, wherein said reinforcing strip is made of silicone.

10. The prosthetic valve of claim 8, wherein said reinforcing strip is made of a layer of pericardial tissue.

11. The prosthetic valve of claim 1, wherein said doubled-over rough side of pericardial tissue is secured together with glue.

12. The prosthetic valve of claim 1, wherein said support body has transverse sewing slits formed therein.

13. The prosthetic valve of claim 12, wherein said slits terminate in circular holes at both ends for reducing mechanical fracture at said ends.

* * * * *